United States Patent
Cook et al.

(10) Patent No.: US 9,173,748 B2
(45) Date of Patent: Nov. 3, 2015

(54) TOROID-SHAPED SPINAL DISC

(75) Inventors: Stephen D. Cook, Baton Rouge, LA (US); Scott Harrington, Westwood, NJ (US)

(73) Assignee: EBI, LLC, Parsippany, NJ (US)

( * ) Notice: Subject to any disclaimer, the term of this patent is extended or adjusted under 35 U.S.C. 154(b) by 527 days.

(21) Appl. No.: 12/839,491

(22) Filed: Jul. 20, 2010

(65) Prior Publication Data

US 2011/0035006 A1     Feb. 10, 2011

Related U.S. Application Data

(60) Provisional application No. 61/232,208, filed on Aug. 7, 2009.

(51) Int. Cl.
*A61F 2/44*     (2006.01)
*A61F 2/30*     (2006.01)

(52) U.S. Cl.
CPC ..... *A61F 2/4425* (2013.01); *A61F 2002/30016* (2013.01); *A61F 2002/3065* (2013.01); *A61F 2002/30563* (2013.01); *A61F 2002/30654* (2013.01); *A61F 2002/30772* (2013.01); *A61F 2002/30841* (2013.01); *A61F 2002/30904* (2013.01); *A61F 2250/0019* (2013.01); *A61F 2310/00017* (2013.01); *A61F 2310/00023* (2013.01); *A61F 2310/00029* (2013.01); *A61F 2310/0097* (2013.01); *A61F 2310/00173* (2013.01); *A61F 2310/00976* (2013.01)

(58) Field of Classification Search
CPC ................. A61F 2/4425; A61F 2230/0065
USPC ................ 623/17.11–17.16; 606/247–249
See application file for complete search history.

(56) References Cited

U.S. PATENT DOCUMENTS

| 4,759,766 | A | * | 7/1988 | Buettner-Janz et al. | ... 623/17.15 |
| 5,284,676 | A | | 2/1994 | Accuntius et al. | |
| 5,401,269 | A | * | 3/1995 | Buttner-Janz et al. | ..... 623/17.15 |
| 5,507,816 | A | * | 4/1996 | Bullivant | ................ 623/17.15 |

(Continued)

FOREIGN PATENT DOCUMENTS

| FR | 2799116 A1 | 4/2001 |
| RU | 2379005 C2 | 1/2010 |

OTHER PUBLICATIONS

International Search Report regarding PCT/US2011/040137 dated May 24, 2012.

(Continued)

*Primary Examiner* — Mary Hoffman
(74) *Attorney, Agent, or Firm* — Schwegman Lundberg & Woessner, P.A.

(57) ABSTRACT

An intervertebral implant for insertion between adjacent vertebral bodies is provided. The intervertebral implant can include a first component. The first component can have a first articulating surface, which can be generally convex. The intervertebral implant can include a second component, which can be generally in the shape of a toroid. The second component can have a second articulating surface. The second articulating surface can be generally concave and articulable with the first articulating surface for retaining motion between the first and second vertebra. The second articulating surface can have a larger radius of curvature than the first articulating surface such that a portion of the first articulating surface extends into an aperture defined by the generally toroid shape.

30 Claims, 5 Drawing Sheets

(56) References Cited

U.S. PATENT DOCUMENTS

| | | | |
|---|---|---|---|
| 5,514,410 A | 5/1996 | Ely et al. | |
| 5,677,061 A | 10/1997 | Ely et al. | |
| 5,782,832 A * | 7/1998 | Larsen et al. | 623/17.11 |
| 5,895,428 A * | 4/1999 | Berry | 623/17.15 |
| 5,899,939 A | 5/1999 | Boyce et al. | |
| 5,899,941 A * | 5/1999 | Nishijima et al. | 623/17.15 |
| 6,113,637 A | 9/2000 | Gill et al. | |
| 6,261,322 B1 | 7/2001 | Despres, III et al. | |
| 6,294,187 B1 | 9/2001 | Boyce et al. | |
| 6,410,087 B1 | 6/2002 | Wilde et al. | |
| 6,436,146 B1 | 8/2002 | Hassler et al. | |
| 6,607,558 B2 | 8/2003 | Kuras | |
| 6,696,073 B2 | 2/2004 | Boyce et al. | |
| 6,770,095 B2 | 8/2004 | Grinberg et al. | |
| 6,793,678 B2 | 9/2004 | Hawkins | |
| 6,969,405 B2 * | 11/2005 | Suddaby | 623/17.12 |
| 7,001,433 B2 | 2/2006 | Songer et al. | |
| 7,083,651 B2 * | 8/2006 | Diaz et al. | 623/17.13 |
| 7,105,030 B2 | 9/2006 | Despres, III et al. | |
| 7,128,761 B2 | 10/2006 | Kuras et al. | |
| 7,153,325 B2 | 12/2006 | Kim et al. | |
| 7,166,131 B2 | 1/2007 | Studer et al. | |
| 7,169,181 B2 | 1/2007 | Kuras | |
| 7,195,644 B2 * | 3/2007 | Diaz et al. | 623/17.13 |
| 7,238,205 B2 | 7/2007 | Karahalios | |
| 7,393,361 B2 | 7/2008 | Zubok et al. | |
| 7,445,640 B2 | 11/2008 | Despres, III et al. | |
| 7,582,115 B2 | 9/2009 | Weber | |
| 7,588,600 B2 | 9/2009 | Benzel et al. | |
| 7,601,174 B2 | 10/2009 | Kelly et al. | |
| 7,618,459 B2 | 11/2009 | Justin et al. | |
| 7,628,815 B2 | 12/2009 | Baumgartner et al. | |
| 7,695,517 B2 | 4/2010 | Benzel et al. | |
| 7,749,272 B2 | 7/2010 | Robie et al. | |
| 7,837,739 B2 | 11/2010 | Ogilvie | |
| 8,268,002 B2 | 9/2012 | Blackwell et al. | |
| 2002/0035400 A1 * | 3/2002 | Bryan et al. | 623/17.15 |
| 2002/0111685 A1 * | 8/2002 | Ralph et al. | 623/17.13 |
| 2003/0074069 A1 * | 4/2003 | Errico et al. | 623/17.14 |
| 2003/0191534 A1 * | 10/2003 | Viart et al. | 623/17.15 |
| 2003/0199981 A1 * | 10/2003 | Ferree | 623/17.15 |
| 2003/0220691 A1 * | 11/2003 | Songer et al. | 623/17.14 |
| 2003/0233146 A1 * | 12/2003 | Grinberg et al. | 623/17.14 |
| 2004/0002762 A1 * | 1/2004 | Hawkins | 623/17.15 |
| 2004/0044410 A1 * | 3/2004 | Ferree et al. | 623/17.13 |
| 2004/0054411 A1 | 3/2004 | Kelly et al. | |
| 2004/0068320 A1 | 4/2004 | Robie et al. | |
| 2004/0143334 A1 | 7/2004 | Ferree | |
| 2005/0021146 A1 * | 1/2005 | de Villiers et al. | 623/17.15 |
| 2005/0027364 A1 | 2/2005 | Kim et al. | |
| 2005/0060034 A1 | 3/2005 | Berry et al. | |
| 2005/0143824 A1 | 6/2005 | Richelsoph et al. | |
| 2005/0165485 A1 * | 7/2005 | Trieu | 623/17.13 |
| 2005/0197706 A1 | 9/2005 | Hovorka et al. | |
| 2005/0228497 A1 * | 10/2005 | Ferree et al. | 623/17.11 |
| 2005/0246022 A1 * | 11/2005 | Zubok et al. | 623/17.11 |
| 2005/0246032 A1 | 11/2005 | Bokros et al. | |
| 2005/0251260 A1 | 11/2005 | Gerber et al. | |
| 2005/0267580 A1 * | 12/2005 | Suddaby | 623/17.12 |
| 2005/0273171 A1 | 12/2005 | Gordon et al. | |
| 2006/0085076 A1 * | 4/2006 | Krishna et al. | 623/17.15 |
| 2006/0149371 A1 | 7/2006 | Marik et al. | |
| 2006/0149372 A1 | 7/2006 | Paxson et al. | |
| 2006/0190079 A1 * | 8/2006 | Istephanous et al. | 623/17.11 |
| 2006/0212122 A1 * | 9/2006 | Perera | 623/17.14 |
| 2006/0235527 A1 | 10/2006 | Buettner-Janz et al. | |
| 2006/0241772 A1 * | 10/2006 | Buettner-Janz et al. | 623/17.15 |
| 2006/0259144 A1 | 11/2006 | Trieu | |
| 2006/0265068 A1 * | 11/2006 | Schwab | 623/17.11 |
| 2006/0287728 A1 | 12/2006 | Mokhtar et al. | |
| 2007/0100455 A1 * | 5/2007 | Parsons | 623/17.14 |
| 2007/0100456 A1 | 5/2007 | Dooris et al. | |
| 2007/0118219 A1 * | 5/2007 | Hyde | 623/17.11 |
| 2007/0154514 A1 | 7/2007 | Demakas et al. | |
| 2007/0156250 A1 | 7/2007 | Seitz et al. | |
| 2007/0168037 A1 * | 7/2007 | Posnick | 623/17.14 |
| 2007/0173941 A1 | 7/2007 | Allard | |
| 2007/0179615 A1 | 8/2007 | Heinz et al. | |
| 2007/0225822 A1 | 9/2007 | Santilli et al. | |
| 2007/0233246 A1 * | 10/2007 | Trieu et al. | 623/17.11 |
| 2007/0270971 A1 | 11/2007 | Trieu et al. | |
| 2007/0288094 A1 * | 12/2007 | Krishna et al. | 623/17.15 |
| 2008/0082173 A1 | 4/2008 | Delurio et al. | |
| 2008/0103597 A1 | 5/2008 | Lechmann et al. | |
| 2008/0183296 A1 * | 7/2008 | Ferree | 623/17.16 |
| 2008/0195212 A1 * | 8/2008 | Nguyen et al. | 623/17.16 |
| 2008/0215155 A1 * | 9/2008 | de Villiers et al. | 623/17.16 |
| 2009/0005872 A1 * | 1/2009 | Moumene et al. | 623/17.16 |
| 2009/0012619 A1 * | 1/2009 | Cordaro et al. | 623/17.15 |
| 2009/0049960 A1 | 2/2009 | Heinsohn | |
| 2009/0054986 A1 * | 2/2009 | Cordaro et al. | 623/17.15 |
| 2009/0088856 A1 | 4/2009 | Levieux | |
| 2009/0234458 A1 | 9/2009 | de Villiers et al. | |
| 2009/0254191 A1 | 10/2009 | Despres, III et al. | |
| 2009/0270986 A1 | 10/2009 | Christensen | |
| 2009/0276051 A1 | 11/2009 | Arramon et al. | |
| 2010/0004746 A1 * | 1/2010 | Arramon | 623/17.15 |
| 2010/0030338 A1 | 2/2010 | Simon | |
| 2010/0137992 A1 * | 6/2010 | Buttner-Janz et al. | 623/17.16 |
| 2010/0256758 A1 | 10/2010 | Gordon et al. | |
| 2010/0268337 A1 | 10/2010 | Gordon et al. | |
| 2010/0298938 A1 | 11/2010 | Humphreys et al. | |
| 2011/0035006 A1 * | 2/2011 | Cook et al. | 623/17.11 |
| 2011/0035010 A1 | 2/2011 | Harrington | |
| 2011/0082556 A1 * | 4/2011 | Duggal et al. | 623/17.16 |
| 2011/0190888 A1 | 8/2011 | Bertele et al. | |
| 2012/0172988 A1 * | 7/2012 | Berger et al. | 623/17.16 |
| 2012/0172991 A1 | 7/2012 | Bertele et al. | |
| 2013/0013069 A1 * | 1/2013 | de Villiers et al. | 623/17.15 |

OTHER PUBLICATIONS

Non-Final Office Action for U.S. Appl. No. 12/840,623, filed Aug. 2, 2012.

Final Office Action for U.S. Appl. No. 12/840,623, filed Nov. 19, 2012.

* cited by examiner

TOROID-SHAPED SPINAL DISC

CROSS-REFERENCE TO RELATED APPLICATIONS

This application claims the benefit of U.S. Provisional Application No. 61/232,208, filed on Aug. 7, 2009. The entire disclosure of the above application is incorporated herein by reference.

INTRODUCTION

The spinal column provides the main support for the body and is made of thirty-three individual bones called vertebrae. There are twenty-four moveable vertebrae in the spine, while the remaining vertebrae are fused. Each individual vertebra can include a posterior vertebral arch for protecting the spinal cord, posterior processes extending from the vertebral arch, and an anterior, drum-shaped vertebral body having superior and inferior endplates. The vertebral body can transmits loads to adjacent bodies via an anterior intervertebral disc and two posterior facets.

The moveable vertebrae are stacked in series and are separated and cushioned by the anterior intervertebral discs. Each intervertebral disc is composed of an outer fibrous ring (i.e., annulus) operating as a pseudo pressure vessel for retaining an incompressible fluid (i.e., nucleus pulposus). The nucleus pulposus is a gel-like substance housed centrally within the annulus and sandwiched between the endplates of the adjacent vertebral bodies. In a healthy disc, the nucleus pulposus acts as a hard sphere seated within the nuclear recess (i.e., fossa) of the vertebral endplates. This sphere operates as the fulcrum (i.e., nuclear fulcrum) for mobility in the spine. Stability is achieved by balancing loads in the annulus and the facet joints.

Degenerative disc disease (DDD) affects the physiology of the disc and may be caused by aging, trauma, or various other factors. DDD results in a reduction in disc height, which in turn, alters the loading pattern in the facets. This altered loading pattern may cause symptomatic degeneration of the facet joints, which may reduce stability and compress the nerves branching out of the spinal column.

Examples of surgical treatments for DDD include spinal fusion and total disc arthroplasty. Total disc arthroplasty may be used to preserve anatomical motion between adjacent vertebral bodies, may reduce stress sustained by adjacent spinal levels, and may slow down disc degeneration.

The present teachings provide a toroid-shaped spinal disc and more particularly, a toroid-shaped spinal disc having superior and inferior components mutually articulating to replicate natural spine movement.

According to one aspect, an intervertebral implant for insertion between adjacent vertebral bodies is provided. The intervertebral implant can include a first component. The first component can have a first articulating surface, which can be generally convex. The intervertebral implant can include a second component, which can be generally in the shape of a toroid. The second component can have a second articulating surface. The second articulating surface can be generally concave and articulable with the first articulating surface for retaining motion between the first and second vertebra. The second articulating surface can have a larger radius of curvature than the first articulating surface such that a portion of the first articulating surface extends into an aperture defined by the generally toroid shape.

According to a further aspect, an intervertebral implant is provided. The intervertebral implant can include a first component. The first component can include a first articulating surface. The first articulating surface can be generally convex with a first radius of curvature. The intervertebral implant can include a second component, which can be generally in the shape of a toroid. The second component can define an aperture, and can include a second articulating surface. The second articulating surface can be generally concave having a second radius of curvature. The second articulating surface can be articulable with the first articulating surface for retaining motion between the first and second vertebra. The first articulating surface and the second articulating surface can directly articulate relative to one another.

Also provided is an intervertebral implant that comprises a first component. The first component can include a first bone engagement surface for engaging a first vertebra and a first articulating surface. The first articulating surface can be generally convex and can have a first radius of curvature. The intervertebral implant can include a second component, which can be generally toroidal in shape. The second component can define an aperture that extends through the second component. The second component can also include a second articulating surface and a second bone engagement surface for engaging a second vertebra. The second articulating surface can be generally concave and can have a second radius of curvature. The second articulating surface can be articulable with the first articulating surface for retaining motion between the first and second vertebra. The second radius of curvature can be larger than the first radius of curvature such that a portion of the first articulating surface extends into the aperture. At least one of the first component and the second component can include an outer shell formed of a first material having a first hardness and an inner core formed of a second material having a second hardness. The second hardness can be different than the first hardness.

Further areas of applicability will become apparent from the description provided herein. It should be understood that the description and specific examples are intended for purposes of illustration only and are not intended to limit the scope of the present teachings.

DRAWINGS

The present invention will become more fully understood from the detailed description and the accompanying drawings, wherein.

DESCRIPTION OF VARIOUS ASPECTS

The following description is merely exemplary in nature and is not intended to limit the present teachings, application, or uses. It should be understood that throughout the drawings, corresponding reference numerals indicate like or corresponding parts and features. Although the following description is related generally to a method and apparatus for use in an anatomy to repair damaged tissue, such as in the case of degenerative disc disease (DDD), it will be understood that the method and apparatus as described and claimed herein, can be used in any appropriate surgical procedure, such as in a spinal fixation or fusion procedure. Therefore, it will be understood that the following discussions are not intended to limit the scope of the present teachings and claims herein.

Figure 1:
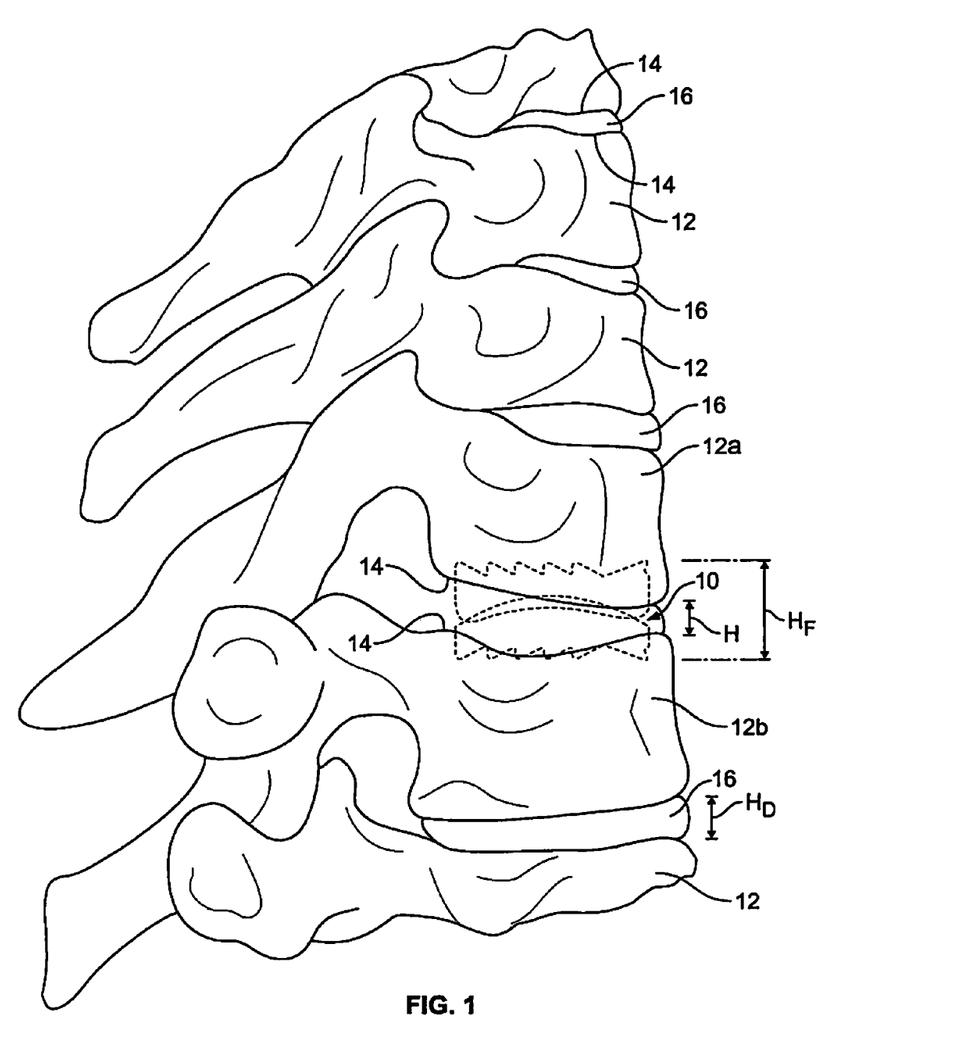
FIG. 1 is a schematic sagittal view of an intervertebral implant according to the present teachings, the intervertebral implant shown implanted in a spine.

Referring to the environmental view of FIG. 1, an exemplary intervertebral implant 10 according to the present teachings is illustrated as positioned or implanted between two adjacent vertebral bodies 12 of a spine. Generally, the intervertebral implant 10 can be positioned between endplates 14 of the vertebral bodies 12 to replace a degenerative disc. In certain applications, the intervertebral implant 10 can be positioned between adjacent vertebral bodies 12 in a cervical region of the spine, however, the intervertebral implant 10 can be used in other anatomical locations, such as the lumbar or thoracic spine. Although a single intervertebral implant 10 is illustrated and described herein as being positioned between a single pair of adjacent vertebral bodies 12, it should be understood that any number of intervertebral implants 10 could be positioned between any suitable pair of vertebral bodies 12. As will be discussed herein, the intervertebral implant 10 can be shaped such that the intervertebral implant 10 provides mutually articulating motion at a reduced implant height, which can allow for more natural motion of a spine of a patient.

With additional reference to FIGS. 2-6, the intervertebral implant 10 can include multiple components configured for mutual articulation to enable anatomical motion between two adjacent vertebral bodies 12. As illustrated in this example, the intervertebral implant 10 can include a first or inferior component 18 and a second or superior component 20. As will become more apparent below, the inferior component 18 and the superior component 20 can be positioned between adjacent vertebral bodies 12, and can be sized to re-establish a disc height $H_D$ associated with a healthy disc 16 to its original dimension. Thus, improved motion and increased stability of the spine may be established.

With continued reference to FIGS. 2-6, at least one of the first and second components 18, 20 can have a generally toroidal shape. As used herein, the phrase "generally toroidal shape" and "generally toroid" shall mean a shape having a main body 22 defining a substantially closed perimeter and an opening or aperture 24. The aperture 24 can be a generally central opening, insofar as it is surrounded by the main body 22. As will be discussed in greater detail herein, in the example of FIGS. 2-6, the superior component 20 can have the generally toroidal shape. In other applications, however, the inferior component 18 can additionally or alternatively have the generally toroidal shape.

The inferior component 18 can comprise an integral component, which can be composed of a suitable biocompatible material, such as a biocompatible metal or polymer. For example, the inferior component 18 can be composed of titanium, cobalt chromium, stainless steel, pyrolytic carbon, etc. If desired, the inferior component 18 can be coated with a suitable biocompatible coating, such as an antibiotic, bone growth material, etc. It should be noted that although the inferior component 18 is described and illustrated herein as comprising a single integral component, the inferior component 18 could comprise multiple components coupled together, if desired. For example, the inferior component 18 could comprise a biocompatible polymer, such as polyethylene, coupled to a biocompatible metal, such as titanium, through a suitable technique. The inferior component 18 can include a first articulating surface 26 and a first bone engagement surface 28. Generally, the first articulating surface 26 can be positioned opposite the first bone engagement surface 28. As will be discussed in greater detail herein, the first articulating surface 26 can cooperate with the superior component 20 to enable relative motion between the inferior component 18 and the superior component 20.

Figure 5:
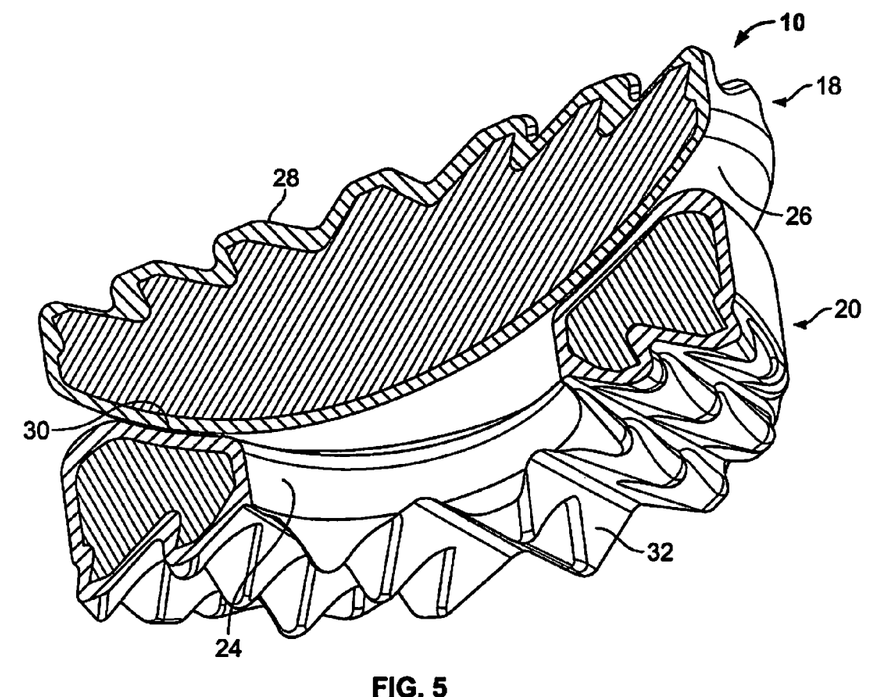
FIG. 5 is a sectional view taken along the line 5-5 of FIG. 4.

In one example, the first articulating surface 26 can be convex, concave or combinations thereof. In the example of FIGS. 2-6, the first articulating surface 26 can be generally convex. In this regard, as best shown in FIG. 5, the first articulating surface 26 can be substantially hemispherical, and can include a first radius of curvature. It should be noted, however, that the first articulating surface 26 can have any shape that enables motion between the inferior component 18 and the superior component 20. For example, the first articulating surface 26 can include distinct radii of curvature that may or may not be concentric.

With reference to FIG. 1, the first bone engagement surface 28 can engage a first vertebra or vertebral body 12a. The first bone engagement surface 28 may be configured in any manner well known in the art to resist expulsion of the intervertebral implant 10 from between the adjacent vertebral bodies 12, and to enable the inferior component 18 to self-center or self-align relative to the vertebral body 12a. In one example, with reference to FIGS. 2-6, the first bone engagement surface 28 can include aggressive multi-angled and self-centering teeth 29 for fixation. The particular structure of the first bone engagement surface 28 will be understood to be beyond the scope of the present teachings.

Figure 2:
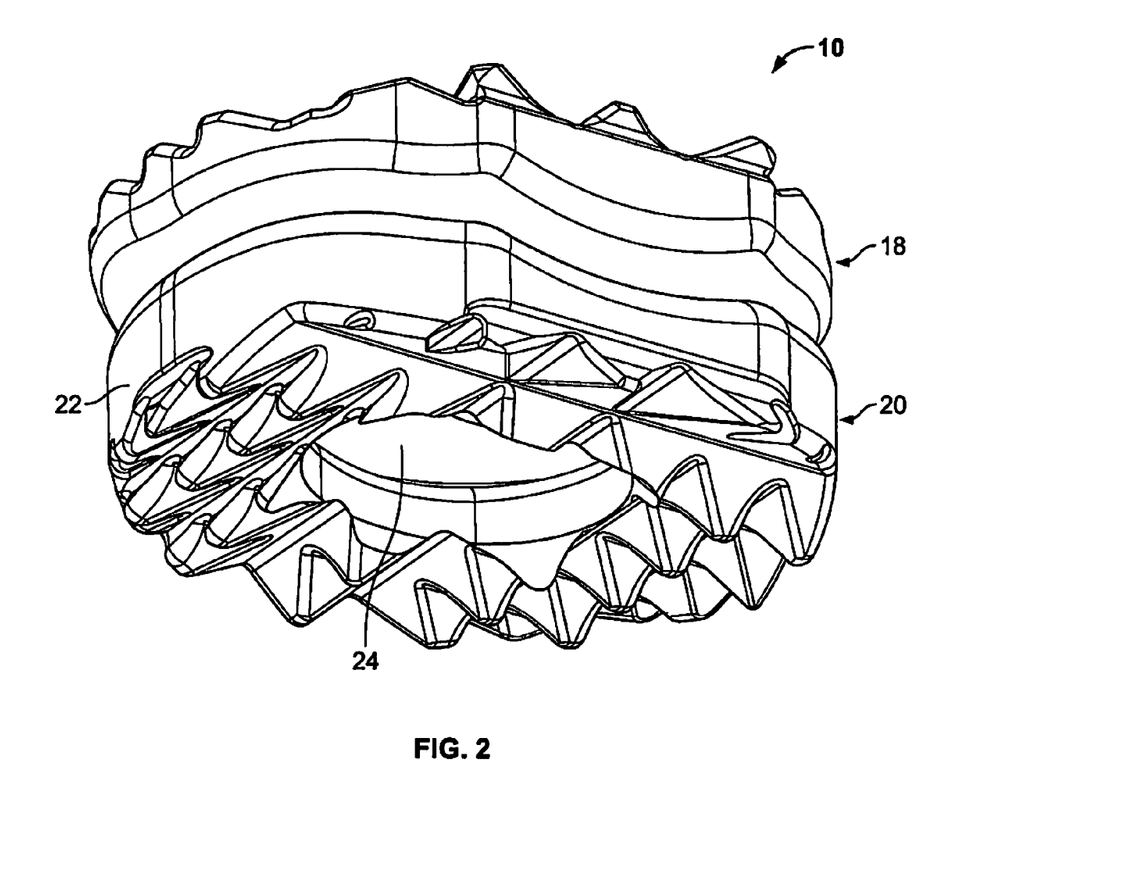
FIG. 2 is a perspective view of the intervertebral implant according to the present teachings.
Figure 2A:
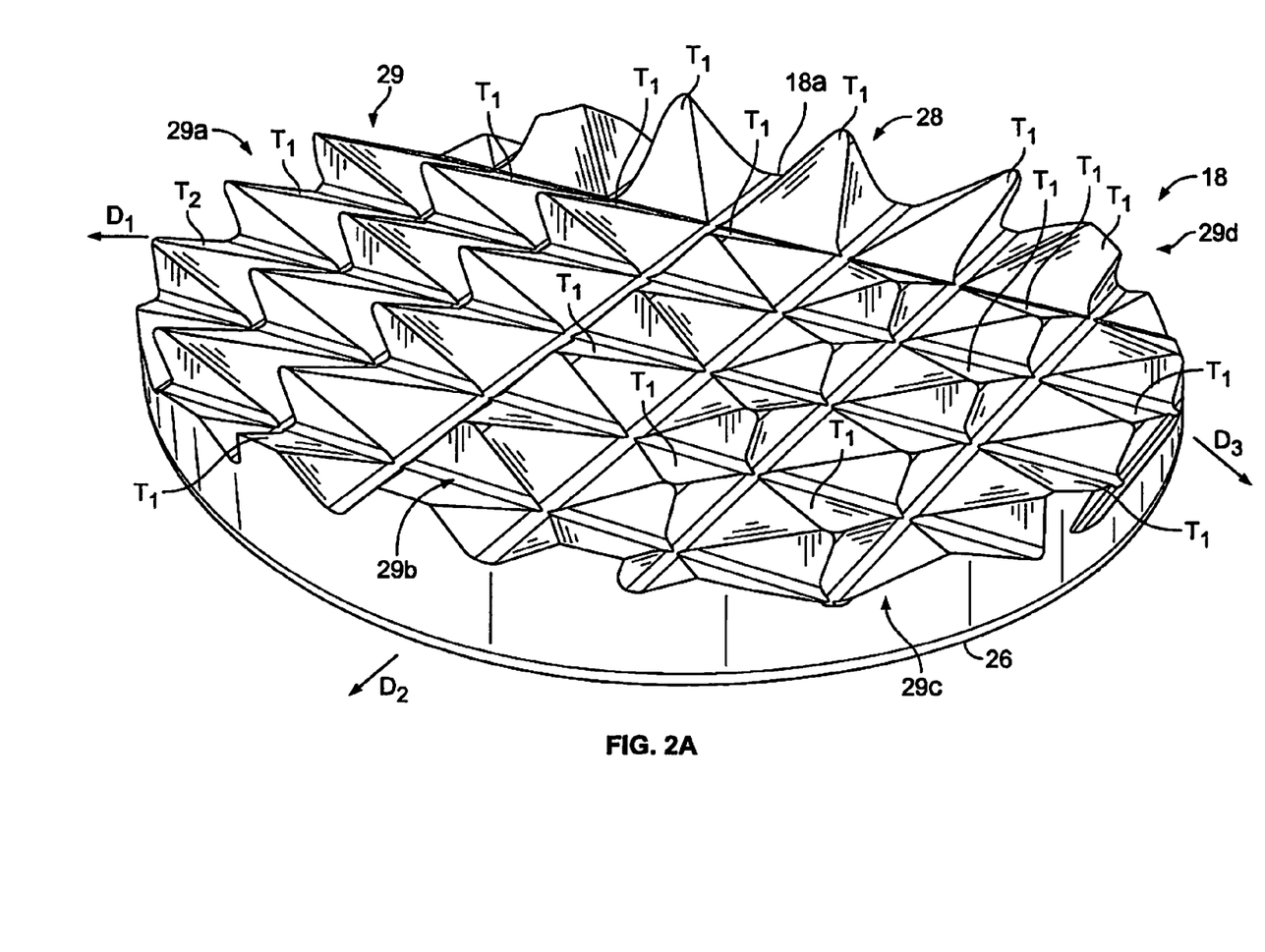
FIG. 2A is a superior perspective view of the intervertebral implant of FIG. 2.

Briefly, however, with reference to FIG. 2A, the teeth 29 of the first bone engagement surface 28 can each include an elongate angled surface T1, which can terminate at a distal point. The distal point can bite into or alter the surface of the vertebral body 12a to couple or fix the inferior component 18 to the vertebral body 12a (FIG. 1). In one example, as shown in FIG. 2A, the various elongate angled surfaces T1 of the teeth 29 can be arranged so as to enable the inferior component 18 to self-center under loads from the adjacent vertebral bodies 12. In this example, the elongate angled surfaces T1 of a first sub-plurality 29a of the teeth 29 can extend in a first direction D1, a second sub-plurality 29b of the teeth 29 can extend in a second direction D2, and a third sub-plurality 29c of the teeth 29 can extend in a third direction D3. Each of the first direction D1, second direction D2 and third direction D3 can be substantially different and can each be directed away from an end 18a of the inferior component 18. The substantially distinct directions of the sub-pluralities 29a, 29b, 29c of the teeth 29 can enable the inferior component 18 to self-center or self-align with the vertebral body 12a. In addition, the inferior component 18 can include a fourth sub-plurality 29d of teeth 29, which can prevent the expulsion of the inferior component 18.

With reference to FIGS. 2-6, the superior component 20 can comprise an integral component, which can be composed of a suitable biocompatible material, such as a biocompatible metal or polymer. For example, the superior component 20 can be composed of titanium, cobalt chromium, stainless steel, pyrolytic carbon, etc. If desired, the superior component 20 can be coated with a suitable biocompatible coating, such as an antibiotic, bone growth material, etc. The superior component 20 can be composed of the same material as the inferior component 18, or can be composed of a different material than the inferior component 18, depending upon desired strength properties, wear properties, etc. It should be noted that although the superior component 20 is described and illustrated herein as comprising a single integral component, the superior component 20 could comprise multiple components coupled together, if desired. For example, the superior component 20 could comprise a biocompatible polymer, such as polyethylene, coupled to a biocompatible metal, such as titanium, through a suitable technique. The superior component 20 can be generally toroidal in shape, and can include a second articulating surface 30, a second bone engagement surface 32 and the aperture 24.

The second articulating surface 30 may be of any shape to cooperate with the first articulating surface 26 to enable relative motion between the inferior component 18 and the superior component 20. Thus, the second articulating surface 30 can comprise any surface that can cooperate with the first articulating surface 26 to enable relative motion between the vertebral bodies 12. In this example, as the first articulating surface 26 can have a generally convex shape, the second articulating surface 30 can have a generally concave shape. It should be noted, however, that the first articulating surface 26 could comprise a generally concave shape, and the second articulating surface 30 could comprise a generally convex shape, if desired. In this example, the second articulating surface 30 can have a generally hemispherical surface, which can define a second radius of curvature. It should be noted, however, that the second articulating surface 30 can have any shape that enables motion between the inferior component 18 and the superior component 20. For example, the second articulating surface 30 could comprise distinct radii of curvature that may or may not be concentric.

Figure 6:
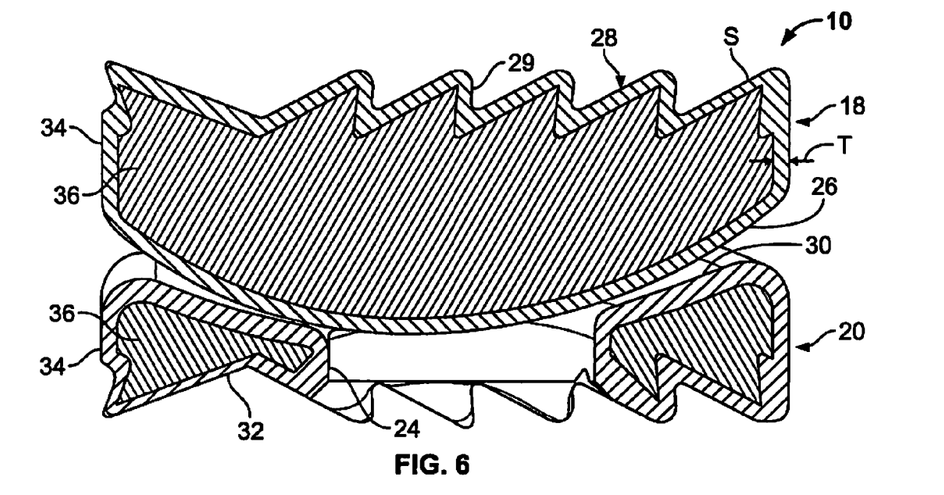
FIG. 6 is a sectional view taken along the line 6-6 of FIG. 4.

In addition, as best shown in FIGS. 5 and 6, the second radius of curvature can be greater than the first radius of curvature, which can establish line contact between the first articulating surface 26 and the second articulating surface 30 of the inferior component 18 and the superior component 20. The line contact may be generally arcuate due to the generally hemispherical surfaces of each of the inferior component 18 and the superior component 20. The line contact between the inferior component 18 and the superior component 20 can maintain stable articulation between the inferior component 18 and the superior component 20. As shown in FIGS. 5 and 6, the intervertebral implant 10 can be devoid of any positive coupling between the inferior component 18 and the superior component 20 while the inferior component 18 and the superior component 20 are in contact with each other along the line of contact.

Further, if the second radius of curvature associated with the superior component 20 is greater than the first radius of curvature associated with the inferior component 18, a portion of the first articulating surface 26 can extend into the opening 24 of the superior component 20. In this manner, the profile of the intervertebral implant 10 may be reduced without compromising the performance of the intervertebral implant 10.

With reference back to FIGS. 1-6, the second bone engagement surface 32 can engage a second vertebra or vertebral body 12$b$. The second bone engagement surface 32 may be configured in any manner well known in the art to resist expulsion of the intervertebral implant 10 from between the adjacent vertebral bodies 12, and to enable the superior component 20 to self-center or self-align relative to the vertebral body 12$b$. As the second bone engagement surface 32 can be similar to the first bone engagement surface 28 described with regard to the inferior component 18, the second bone engagement surface 32 will not be discussed in great detail herein, and the same reference numerals will be used to denote the same or similar components. Briefly, however, in this example, the second bone engagement surface 32 can include the teeth 29, which can self-center or self-align the superior component 20 relative to the vertebral body 12$b$, while resisting the expulsion of the superior component 20. It should be noted that the second bone engagement surface 32 can include any suitable bone engagement surface known in the art, such as spikes, barbs, etc.

Figure 3:
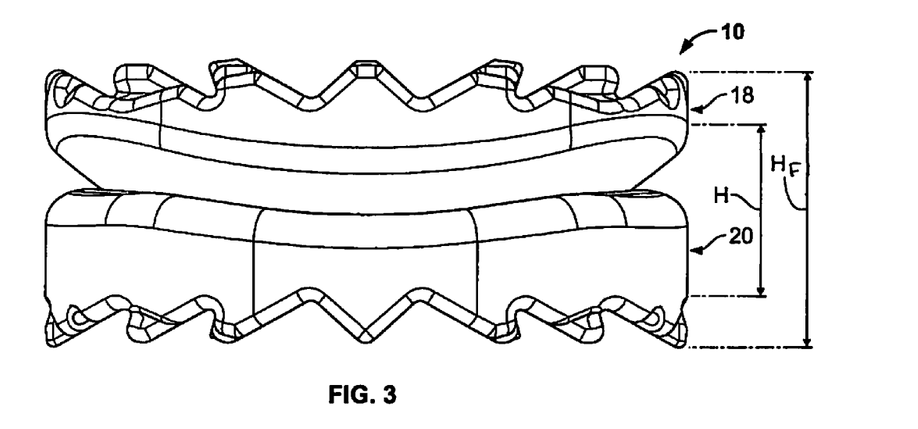
FIG. 3 is an anterior end view of the intervertebral implant of FIG. 2.
Figure 4:
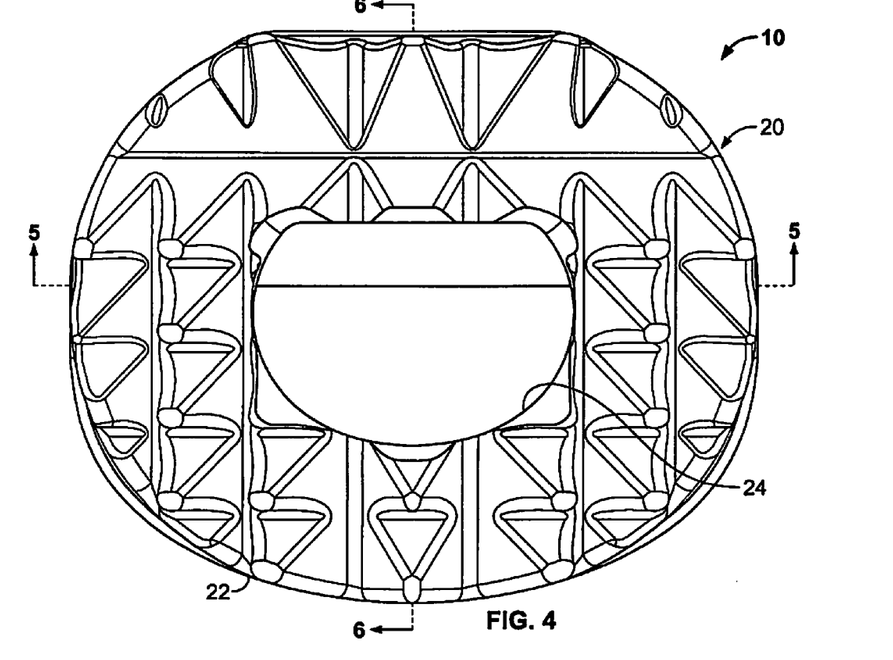
FIG. 4 is an inferior view of the intervertebral implant of FIG. 2.

With reference to FIGS. 3-6, the aperture 24 can be formed through the superior component 20 so as to extend from the second articulating surface 30 to the second bone engagement surface 32. The aperture 24 can generally receive a portion of the first articulating surface 26 of the inferior component 18, which can reduce an implant height H of the intervertebral implant 10, as will be discussed in greater detail herein (FIG. 3). It will be understood, however, that the aperture 24 need not extend through the superior component 20. In this regard, the opening 24 can extend through only a portion of the superior component 20. In the case of the opening 24 extending only partially through the superior component 20, the opening 24 may intersect the second articulating surface 30, but may extend only substantially through the superior component 20. In other words, the aperture 24 can be formed as a depression within the second articulating surface 30 so that the aperture 24 can receive the first articulating surface 26 of the inferior component 18 to reduce the height H of the intervertebral implant 10, but the aperture 24 need not extend all the way through the superior component 20.

In one of various examples, with particular reference to FIGS. 5 and 6, at least one of the inferior component 18 and the superior component 20 can comprise a shell 34 and an inner core 36. By constructing at least one of the inferior component 18 and the superior component 20 to have a shell 34 and a inner core 36, the inferior component 18 and/or superior component 20 can have increased wear properties while providing a degree of compressibility. In other words, the use of a shell 34 and an inner core 36 can provide the benefits of two materials through a single integral component.

In this regard, the shell 34 can be constructed of a first material having a first hardness. As the shell 34 can form an outer surface S of the inferior component 18 and/or the superior component 20, the shell 34 can have a suitable hardness that enables the inferior component 18 and/or the superior component 20 to engage the vertebral bodies 12 and articulate relative to each other. In addition, the shell 34 can have a thickness T. The thickness T of the shell 34 can coordinate with the hardness of the shell 34 to facilitate the desired wear characteristics and to enable a degree of compressibility for the inferior component 18 and/or the superior component 20. It can be desirable to have a degree of compressibility for the inferior component 18 and/or the superior component 20 as it enables the patient to undergo some flexion of the spine, thereby providing the patient with more natural motion.

With continued regard to FIGS. 5 and 6, the inner core 36 can be constructed of a second material having a second hardness. As the inner core 36 can be wholly retained within the shell 34, the second hardness of the inner core 36 can be distinct from the first hardness of the shell 34. In this example, the first hardness of the shell 34 can be greater than the second hardness of the inner core 36. For example, the shell 34 can be constructed of pyrolytic carbon and the inner core 36 can be constructed of graphite. The use of the pyrolytic carbon for the shell 34 can protect the inferior component 18 and/or the superior component 20 from wear, while the use of graphite for the inner core 36 can provide a degree of compressibility for the inferior component 18 and/or the superior component 20.

In the example of FIGS. 2-6, each of the inferior component 18 and the superior component 20 can include the shell 34 and the inner core 36, however, it will be understood that only one of the inferior component 18 or the superior component 20 or none of the inferior component 18 and the superior component 20 could include the shell 34 and inner core 36.

With reference to FIGS. 5 and 6, in order to assemble the intervertebral implant 10, the inferior component 18 can be aligned with the superior component 20 such that the first articulating surface 26 is at least partially received within the aperture 24, and the first articulating surface 26 is in contact with the second articulating surface 30. Then, with the intervertebral implant 10 assembled, the intervertebral implant 10 can be inserted into the anatomy. As the insertion of the intervertebral implant 10 is generally well known in the art, the insertion of the intervertebral implant 10 will not be discussed in great detail herein. Briefly, however, in order to insert the intervertebral implant 10 into the anatomy, such as between adjacent vertebral bodies 12 (FIG. 1), the anatomy can be prepared to receive in the intervertebral implant 10. In this regard, surgical access can be made to an area adjacent to the vertebral bodies 12. For example, surgical access can be obtained via a minimally invasive surgical procedure or a posterior unilateral open procedure.

With access gained to the surgical site, the surgical site can be prepared to receive the intervertebral implant 10. Then, the intervertebral implant 10 can be coupled to a suitable instrument, which can guide the intervertebral implant 10 into the space defined between the adjacent vertebral bodies 12. With the intervertebral implant 10 properly positioned between the vertebral bodies 12, the intervertebral implant 10 can restore the space between the adjacent vertebral bodies 12 to a height substantially similar to the height $H_D$ of a healthy disc 16.

In this regard, with reference to FIG. 1, when the intervertebral implant 10 is positioned between adjacent vertebral bodies 12, the implant height H of the intervertebral implant 10 can be substantially similar to the height $H_D$ of a healthy disc 16 so as to restore substantially normal function to the spine of the patient. In one example, the implant height $H_D$ of the intervertebral implant 10 can range from about 4.0 millimeters (mm) to about 9.0 millimeters (mm). In certain particular applications, the implanted height H of the interverterbral implant 10 may be no greater than 8.5 millimeters (mm). It will be understood that the implanted height H of the intervertebral implant 10 may be different than a height $H_F$ associated with an assembled intervertebral implant 10, as the teeth 29 of the first bone engagement surface 28 and the second bone engagement surface 32 may bite into and be substantially received into the respective vertebral body 12. Further, the implant height H of the intervertebral implant 10 can be adjusted for optimal fit between the adjacent vertebral bodies 12, and the implant height H can depend upon the particular anatomical conditions of the patient. Thus, in certain instances, it may be desirable to provide a kit of various intervertebral implants 10, each having a distinct implant height H.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. An intervertebral implant comprising:
    a first component having a first articulating surface, the first articulating surface being generally convex; and
    a second component being generally in the shape of a toroid and having a second articulating surface, the second articulating surface being generally concave and articulable with the first articulating surface for retaining motion between a first vertebra and a second vertebra;
    wherein the second articulating surface has a larger radius of curvature than the first articulating surface such that a portion of the first articulating surface extends into an aperture defined by the generally toroid shape, the aperture extending into the second articulating surface and a portion of the first articulating surface abutting the second articulating surface at a location defining a perimeter of the aperture; and
    wherein the first component is a single component, the first component and the second component define a first vertebral engaging surface and a second vertebral engaging surface, respectively, and the first vertebral engaging surface and the second vertebral engaging surface each include a plurality of protrusions.

2. The intervertebral implant of claim 1, wherein the larger radius of curvature of the second articulating surface defines an arcuate line of contact between the first articulating surface and the second articulating surface.

3. The intervertebral implant of claim 1, wherein the aperture defined by the second component extends completely through the second component.

4. The intervertebral implant of claim 1, wherein the first articulating surface is generally hemispherical.

5. The intervertebral implant of claim 1, wherein the second component further comprises a single integral component.

6. The intervertebral implant of claim 1, wherein the first vertebral engaging surface and the second vertebral engaging surface each include a plurality of teeth.

7. The intervertebral implant of claim 6, wherein each of the plurality of teeth comprise an angled surface so as to allow the respective first component and second component to self-center in response to loads applied via the first and second vertebrae.

8. The intervertebral implant of claim 7, wherein each of the plurality of teeth include a subplurality of teeth that prevent expulsion of each of the respective first component and second component from the first and second vertebrae.

9. An intervertebral implant comprising:
    a first component including a first articulating surface, the first articulating surface being generally convex with a first radius of curvature; and
    a second component being generally in the shape of a toroid and defining an aperture, the second component including a second articulating surface, the second articulating surface being generally concave having a second radius of curvature, the second articulating surface being articulable with the first articulating surface for retaining motion between a first vertebra and a second vertebra, the aperture extending into the second articulating surface and a portion of the first articulating surface abutting the second articulating surface at a location defining a perimeter of the aperture;
wherein the first articulating surface and the second articulating surface directly articulate relative to one another; and
wherein the first component is a single component, the first component and the second component define a first vertebral engaging surface and a second vertebral engaging surface, respectively, and the first vertebral engaging surface and the second vertebral engaging surface each include a plurality of protrusions.

10. The intervertebral implant of claim 9, wherein the first radius of curvature and the second radius of curvature are different.

11. The intervertebral implant of claim 9, wherein the aperture extends completely through the second component.

12. The intervertebral implant of claim 9, wherein at least one of the first component and the second component include an inner core and an outer shell entirely enclosing the inner core, the outer shell being formed of a first material having a first hardness, the inner core being formed of a second material having a second hardness.

13. The intervertebral implant of claim 12, wherein the second hardness is less than the first hardness.

14. The intervertebral implant of claim 12, wherein the outer shell is formed of a pyrolytic carbon and the inner core is formed of graphite.

15. An intervertebral implant comprising:
a first component including a first bone engagement surface for engaging a first vertebra and a first articulating surface, the first articulating surface being generally convex with a first radius of curvature; and
a second component being generally toroidal in shape and defining an aperture that extends through the second component, the second component including a second articulating surface and a second bone engagement surface for engaging a second vertebra, the second articulating surface being generally concave and having a second radius of curvature, the second articulating surface being articulable with the first articulating surface for retaining motion between the first and second vertebra and the second radius of curvature being larger than the first radius of curvature such that a portion of the first articulating surface extends into the aperture;
wherein at least one of the first component and the second component include an inner core and an outer shell entirely enclosing the inner core, the outer shell defining the first articulating surface or the second articulating surface and being formed of a first material having a first hardness; the inner core being formed of a second material having a second hardness that is less than the first hardness.

16. The intervertebral implant of claim 15, wherein the outer shell is formed from a pyrolytic carbon.

17. The intervertebral implant of claim 15, wherein the larger radius of curvature of the second articulating surface defines an arcuate line of contact between the first articulating surface and the second articulating surface.

18. The intervertebral implant of claim 15, wherein the first component and the second component each further comprise a single integral component, and the first component and the second component directly articulate relative to each other.

19. The intervertebral implant of claim 1, wherein the first articulating surface is continuously smooth and devoid of any obstructions.

20. The intervertebral implant of claim 1, wherein the implant is devoid of any positive coupling between the first and second components.

21. The intervertebral implant of claim 1, wherein the second component has an inner perimeter and an outer perimeter and further wherein the concave second articulating surface extends at least substantially an entire distance between the inner and outer perimeters.

22. The intervertebral implant of claim 21, wherein the first component has an outer perimeter generally corresponding in size and shape to the outer perimeter of the second component.

23. The intervertebral implant of claim 9, wherein the first articulating surface is continuously smooth and devoid of any obstructions.

24. The intervertebral implant of claim 9, wherein the implant is devoid of any positive coupling between the first and second components.

25. The intervertebral implant of claim 9, wherein the second component has an inner perimeter and an outer perimeter and further wherein the concave second articulating surface extends at least substantially an entire distance between the inner and outer perimeters.

26. The intervertebral implant of claim 25, wherein the first component has an outer perimeter generally corresponding in size and shape to the outer perimeter of the second component.

27. The intervertebral implant of claim 15, wherein the first articulating surface is continuously smooth and devoid of any obstructions.

28. The intervertebral implant of claim 15, wherein the implant is devoid of any positive coupling between the first and second components.

29. The intervertebral implant of claim 15, wherein the second component has an inner perimeter and an outer perimeter and further wherein the concave second articulating surface extends at least substantially an entire distance between the inner and outer perimeters.

30. The intervertebral implant of claim 29, wherein the first component has an outer perimeter generally corresponding in size and shape to the outer perimeter of the second component.

* * * * *